US011096655B2

United States Patent
De Beni et al.

(10) Patent No.: US 11,096,655 B2
(45) Date of Patent: Aug. 24, 2021

(54) METHOD FOR POSTURAL INDEPENDENT LOCATION OF TARGETS IN DIAGNOSTIC IMAGES ACQUIRED BY MULTIMODAL ACQUISITIONS AND SYSTEM FOR CARRYING OUT THE METHOD

(71) Applicants: Esaote S.p.A., Genoa (IT); MedCom GmbH, Darmstadt (DE)

(72) Inventors: Stefano De Beni, Genoa (IT); Velizar Kolev, Darmstadt (DE)

( * ) Notice: Subject to any disclaimer, the term of this patent is extended or adjusted under 35 U.S.C. 154(b) by 542 days.

(21) Appl. No.: 15/972,197

(22) Filed: May 6, 2018

(65) Prior Publication Data

US 2018/0325489 A1  Nov. 15, 2018

(30) Foreign Application Priority Data

May 10, 2017 (EP) ..................................... 17170367

(51) Int. Cl.
*A61B 8/08* (2006.01)
*G01R 33/48* (2006.01)
(Continued)

(52) U.S. Cl.
CPC .......... *A61B 8/0833* (2013.01); *A61B 5/0035* (2013.01); *A61B 5/0064* (2013.01);
(Continued)

(58) Field of Classification Search
None
See application file for complete search history.

(56) References Cited

U.S. PATENT DOCUMENTS 7,801,708 B2 * 9/2010 Unal .................. G06K 9/00214
703/2
2009/0097778 A1 * 4/2009 Washburn ................ G06T 7/33
382/294
(Continued)

FOREIGN PATENT DOCUMENTS

WO   2012112907   8/2012
WO   2016201341   12/2016

OTHER PUBLICATIONS

Conley et al., "Realization of a biomechanical model-assisted image guidance system for breast cancer surgery using supine MRI", Int J CARS, vol. 10, pp. 1985-1996, Jun. 2015. (Year: 2015).*
(Continued)

*Primary Examiner* — Katherine L Fernandez
(74) *Attorney, Agent, or Firm* — Themis Law

(57) ABSTRACT

A method for postural independent location of targets in diagnostic images acquired by multimodal acquisitions, compensating for deformation of soft tissues due to changing posture, includes generating a transition of a digital image of the inside of a target region from a first to a second position by correlating the position of markers placed on the external surface of the target region in a digital image of the inside of the target region and in a digital representation of the external surface of the target region acquired by optically scanning the external surface; and at a later time registering the diagnostic image of the inside of the target region, transitioned into the second position, with a diagnostic image of the same target region acquired with the target region in the second position by matching a second representation of the external surface of the target region in the second position without markers with the diagnostic image of the inside of the target region transitioned into the second position.

4 Claims, 11 Drawing Sheets

(51) Int. Cl.
| | |
|---|---|
| *A61B 5/00* | (2006.01) |
| *A61B 5/055* | (2006.01) |
| *A61B 6/00* | (2006.01) |
| *A61B 6/04* | (2006.01) |
| *G16H 30/40* | (2018.01) |
| *G16H 40/63* | (2018.01) |
| *G01R 33/56* | (2006.01) |
| *A61B 8/00* | (2006.01) |
| *A61B 17/34* | (2006.01) |
| *A61B 90/00* | (2016.01) |

(52) U.S. Cl.
CPC ............ *A61B 5/055* (2013.01); *A61B 6/0492* (2013.01); *A61B 6/5247* (2013.01); *A61B 8/0825* (2013.01); *A61B 8/0841* (2013.01); *A61B 8/5261* (2013.01); *G01R 33/4808* (2013.01); *G01R 33/4814* (2013.01); *G01R 33/4822* (2013.01); *G16H 30/40* (2018.01); *G16H 40/63* (2018.01); *A61B 5/4312* (2013.01); *A61B 6/502* (2013.01); *A61B 8/406* (2013.01); *A61B 2017/3413* (2013.01); *A61B 2090/364* (2016.02); *A61B 2090/374* (2016.02); *A61B 2090/378* (2016.02); *A61B 2090/3908* (2016.02); *A61B 2090/3937* (2016.02); *A61B 2090/3954* (2016.02); *A61B 2090/3983* (2016.02); *A61B 2090/3995* (2016.02); *G01R 33/5608* (2013.01)

(56) References Cited

U.S. PATENT DOCUMENTS

| | | | |
|---|---|---|---|
| 2014/0044333 A1* | 2/2014 | Barth, Jr. | .................. G06T 7/33 382/131 |
| 2015/0196282 A1 | 7/2015 | Ishida | |

OTHER PUBLICATIONS

Pallone et al., "Supine Breast MRI and 3D Optical Scanning: A Novel Approach to Improve Tumor Localization for Breast Conserving Surgery", Ann Surg Oncol, vol. 21, pp. 2203-2208, 2014. (Year: 2014).*

Han et al., "A Nonlinear Biomechanical Model Based Registration Method for Aligning Prone and Supine MR Breast Images", IEEE Transactions on Medical Imaging, vol. 33, No. 3, pp. 682-694, Mar. 2014. (Year: 2014).*

Lago, MA, Breast prone-to-supine deformation and registration using a Time-of-Flight camera, Biomedical Robotics and Biomechatronics (BIOROB), 2012 4th IEEE RAS&EMBS International Conference On, IEEE, Jun. 24, 2012, pp. 1161-1163 pp. 1162, 11.

European Patent Office, European Search Report, Application No. EP 17 17 0367, dated Nov. 18, 2017.

* cited by examiner

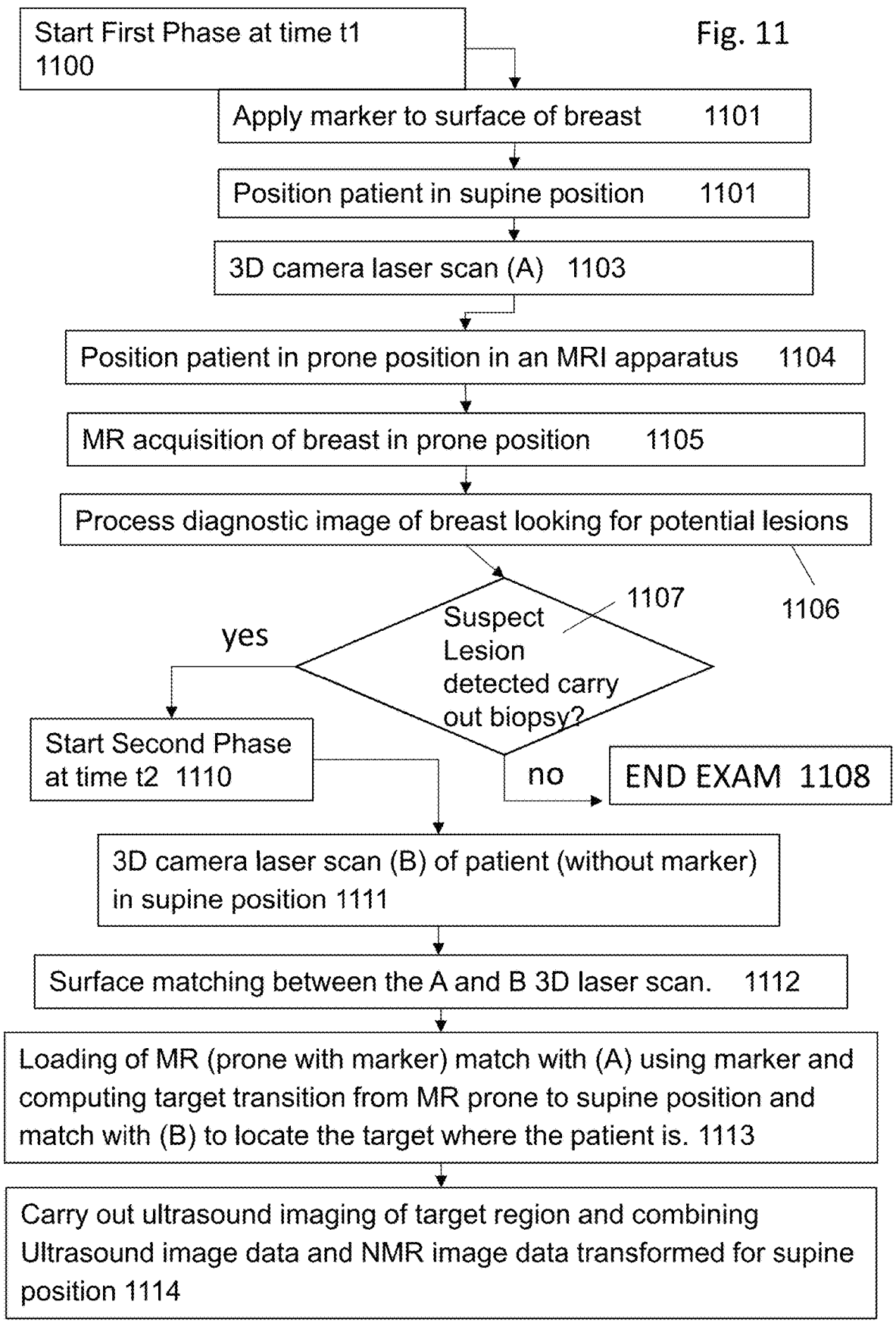

METHOD FOR POSTURAL INDEPENDENT LOCATION OF TARGETS IN DIAGNOSTIC IMAGES ACQUIRED BY MULTIMODAL ACQUISITIONS AND SYSTEM FOR CARRYING OUT THE METHOD

FIELD OF THE INVENTION

The invention relates to a method and related system for postural independent location of targets in diagnostic imagines acquired by multimodal acquisitions.

BACKGROUND OF THE INVENTION

Multimodal image acquisition has been used, for example, in biopsy needle guiding techniques requiring high quality and high definition of the morphological structure of an imaged region of interest (ROI) in an object and at the same time a real time imaging of the relative position of the target and of the biopsy needle.

One example of such method and system is described in EP2147636. This document discloses a device and method for guiding surgical tools by ultrasonic imaging having means for acquiring a time sequence of 3D ultrasonic images of a target area, means for determining and tracking the position and orientation of a surgical tool and means for defining the direction of a characteristic axis of the tool corresponding to the detected position and orientation of the tool. The device further is provided with means for determining the position of a working end of the tool along the characteristic axis, means for determining the relative position in space of each 3D image and the direction of the characteristic axis corresponding to each 3D image, and means for generating a 2D image defined by an image plane that intersects the corresponding 3D image of said time sequence.

Multimodal techniques are also applied when in the district to be imaged there are static tissues and moving tissues, such as moving organs or body fluids. In this case the volume acquisitions of a ROI for generating volumetric high resolution images of the ROI require long acquisition times which are longer than the frequency of motion of the fluids and or of the organ in the ROI. In this kind of conditions at least one volumetric image acquired by a high resolution and high definition imaging technique is combined with a registered volumetric or two-dimensional ultrasound image which can be acquired in real time. The time dependent behaviour of an organ in a ROI imaged by the ultrasound technique can be registered and combined with the volumetric high definition morphological image obtaining a final image integrating the information of the images according to both image acquisition modes or techniques.

One of the major problems in combining information of images of the same ROI which has been acquired by different imaging modes or techniques consist in the fact that the ROI or at least part of the ROI is subjected to movements. When the target object or the ROI is a soft tissue or is located in a soft tissue, the posture of the patient during examination may cause changes in shape of the target object or of the ROI. In multimodal imaging this may cause problems since different imaging techniques may require different examination postures of a patient for imaging the same target object or the same ROI. Further problems relating changes in shape of the target object or of the ROI in a target object may also occurred in carrying out follow up imaging sessions al later times than a first acquisitions. These follow up imaging sessions may be carried at a distance of days or weeks from the earlier ones.

A particular case relates to the multimodal imaging of targets inside a ROI, for example of suspect lesions which has to be subjected to biopsy or to other kind of treatment. In this case the postural changes of the patient from a first volumetric image acquisition with one imaging technique to a following imaging technique needed for example to trace and guide a treatment tool and which second imaging technique requires a different posture of the patient may render difficult to recognize and identify the target object, for example the lesion in the image acquired with the second imaging technique and to correctly register the images acquired with the first and the second imaging technique. As a result the needle guidance may be compromised or at least not so precise to direct the needle onto the target object.

One very relevant special case relates to taking biopsy probes of a target identified in an NMR image under guidance of the biopsy needle by ultrasound imaging. In this case the NMR imaging session requires the patient to be positioned prone, while the ultrasound imaging for guiding the biopsy needle requires the patient to be positioned supine as it is shown in FIG. 1. The breast will be subject to changes in shape when passing from the prone to the supine position or viceversa. This deformation introduces errors in the registering process of the NMR image with the ultrasound images and thus in the precise location of the target to be subjected to biopsy in the combined NMR and Ultrasound image.

SUMMARY OF THE INVENTION

According to a first object, the present invention provides a method for postural independent location of targets in diagnostic imagines acquired by multimodal acquisitions, this method allowing to compensate for the deformation to which soft tissues are subject by changing posture of the patient and particularly in the conditions in which such deformations have an effect on the external visible shape of parts of the body or of the object.

According to a further object, the invention provides for a simple method which is easy to be carried out and which is reliable.

A further object of the present invention is providing a method for biopsy of a target identified in an NMR image by ultrasound guiding a biopsy needle.

Still another object of the present invention is providing a system for carrying out a method for postural independent location of targets in diagnostic imagines acquired by multimodal acquisitions Another object of the present invention is providing a system for carrying out a method for biopsy a target identified in an NMR image by guiding a biopsy tool by means of ultrasound imaging.

According to a first aspect, a method according to the present invention comprise the steps of generating a transition of a digital image of the inside of a target region from a first to a second position of the target region by correlating the position of markers placed on the external surface of the target region in the digital image of the inside of the target region and in a digital representation of the surface of the target region acquired by optical scanning the surface; and at a later time, registering the diagnostic image of the inside of the target region, which has been transitioned into the second position, with a diagnostic image of the same target region acquired with the target region in the second position by matching a second representation of the external surface of the target body in the second position without markers with the diagnostic image of the inside of the target region which has been transitioned into the second position.

According to an embodiment, the present invention provides for a method for postural independent location of targets in diagnostic imagines acquired by multimodal acquisitions comprising the following steps:

Placing markers on the external surface of an anatomical target region which must be subjected to diagnostic imaging;

The markers being responsive to optical radiation and to at least one further imaging technique for imaging the inside of the target region;

Acquiring by optically scanning a target region a first digital representation of the external surface of the target region together with the markers with the target region in a first position in space;

Acquiring a diagnostic image of the inside of the target region or of a ROI inside the target region together with the markers by the further imaging technique with the target region in a second position in space;

Performing a correlation between the diagnostic image and the optical representation of the external surface by correlating the marker positions in the diagnostic image and on the representation of the surface of the target region;

At a later time acquiring by optically scanning a target region a second digital representation of the external surface of the target region without the markers and with the target region in the first position;

Carrying out a surface matching between the first and second digital representations of the external surface of the target region;

Computing the transition of the digital image of the inside of the target region form the second position in space to the first position in space by applying the correlation and obtaining a digital image of the inside of the target region transitioned to the first position;

Matching the digital image of the inside of the target region transitioned to the first position with the second digital representation of the external surface of the target region to locate the target;

Carrying out ultrasound imaging of the target region with the target region in the first position in space and registering the ultrasound image with the digital image of the inside of the target region transitioned to the first position and matched with the second digital representation of the external surface in the first position.

According to an embodiment herein, the diagnostic imaging technique can be selected form one of the following options: MRI, CT, CBCT, PET and Ultrasound.

The diagnostic image of the inside of the target region is preferably a 3D-image of a certain volume.

According to an embodiment herein the digital representation of the external surface of the target region either with or without markers is acquired by a 3D laser scan of the surface.

According to a further embodiment herein registration and correlation of the marker position may be computed by means of several techniques and/or surface matching and/or registration of the digital image acquired by the two different imaging techniques is carried out by means of one of the following methods or by combination of the methods such as intensity based registration methods comparing intensity patterns in images via correlation metrics, feature-based methods find correspondence between image features such as points, lines, and contours, registration methods using rigid or elastic transformations such as transformations using radial basis functions, transformations using physical continuum models as fluid dynamic models of viscous fluids or method based on diffeomorphisms models, methods using similarity measures such as cross-correlation, mutual information sum of squared intensity differences and ratio image uniformity, methods based on measure matching, curve matching, surface matching vi mathematical currents and varifolds. The list gives only some examples of the models and method used to carry out the image processing steps of the method according to the present invention and the possible methods and techniques for carrying out the correlation between the marker positions, computing the transition equations and matching surfaces and also registering images shall not be considered limited with the above listed ones.

According to a further embodiment, the method of the present invention is directed to navigating in real time the breast by using and combining information of a 3D NMR image with the information acquired in a second time an in real time by ultrasound imaging, the method providing the following steps:

Placing one or more markers on the external surface of the breast according to a predefined pattern;

Acquiring a digital representation of the breast with the patient in a supine position by scanning the breast with a 3D laser camera scanner;

Acquiring an NMR image of the breast with the markers with the patient in prone position;

At a later time for registering ultrasound images of the breast acquired in a supine position of the patient with the NMR images of the breast acquired in the prone position of the patient the following step are carried out:

Acquiring a second digital representation of the breast with the patient in a supine position by scanning the breast without the markers with a 3D laser camera scanner;

Carrying out a surface matching between the first and the second digital representation of the external surface of the breast;

Correlating the position of the markers in the NMR image with markers in prone position of the patient with the position of the markers in the first digital representation of the external surface of the breast with markers in the supine position of the patient;

Computing a transition of the target identified in the NMR image from the position in the breast related to the prone position of the patient to the position of the target in the breast related to a supine position of the patient by using the correlation of the marker positions in the prone and supine position of the patient according to the previous step;

Matching the NMR image with the transitioned from the prone position to the supine position with the second image of the breast acquired without markers to locate the target in the breast being in the supine position in which the ultrasound imaging of the breast is carried out;

Carrying out ultrasound imaging of the breast in the supine position and locate the target in the ultrasound image by combining the ultrasound image with the NMR image transitioned from the prone to the supine position and matched with the second digital representation of the surface of the breast.

According to a further variant embodiment, the correlation between markers position in the digital image of the inside of the target region such as the breast and in the first representation of the surface of the target region may be calculated and stored in a patient file in a patient database and can be retrieved at a later time for carrying out the further steps of the method as disclosed in the description one or more of the above embodiments.

According to a further variant embodiment the correlation may be in the form of a function or of a table and may be used for each of the following ultrasound imaging examinations executed on the patient.

According to a further embodiment which may be provided in combination of any one of the previous variant embodiments, the us ultrasound images are used to trace and guide in real time a biopsy tool during execution of a biopsy.

These steps may be carried out according for example the method taught by EP2147636.

According to an embodiment, the method according to one or more of the preceding embodiments may provide the following additional steps:

providing a reference system in which the target region is placed;

tracing the position of the ultrasound probe and of the ultrasound image slice relatively to the reference system;

registering the NMR image with the reference system;

combing the ultrasound image slice with the corresponding image slice of the NMR image.

The registration of the NMR image with the reference system may be obtained by defining as the reference system the reference system of the first digital representation of the surface of the target region.

According to a further embodiment the registration of the ultrasound images with the reference system defined as the reference system of the first digital representation of the surface of the target region may be carried out by matching the second digital representation of the target region.

Referred to the embodiment in which the representation of the surface of the target region is a 3D scan carried out by a 3D laser camera, the reference system may be chosen as the one related to the 3D scan of the surface of the target region.

According to a further aspect the present invention relates to a system for carrying out postural independent location of targets in diagnostic imagines acquired by multimodal acquisitions, the system comprising:

An imaging unit for acquiring 3D digital representations of the surface of a target region;

An apparatus for acquiring diagnostic images inside the target region;

An ultrasound system;

A processing unit configured to receive 3D representations of the target region and diagnostic images of the inside of the target region;

Two or more markers to be placed on the surface of the target region;

The processing unit being configured to correlate the position of markers on a 3D representation of the target region of a patient and on the diagnostic image of the inside of the target region and to store the result of the correlation in a memory;

The processing unit being configured to carry out image registration of a diagnostic image of the inside of the target region with a representation of the surface of the target region acquired both with markers on the target region and image registration of at least one further representation of the surface of the target region acquired without markers at the later time and to register an ultrasound image with the NMR image based on the registrations carried out matching the NMR image with the representations of the external surface of the target region.

As a scanner for acquiring the digital representations of the target region an embodiment provides for a 3D-laser camera.

The MRI imaging apparatus may be part of the system or the system is provided only with means for reading and storing or for remotely downloading the acquired NMR images. In this case the MRI apparatus is a separate apparatus.

According to a variant embodiment the system in its minimum configuration comprises:

an ultrasound system for acquiring ultrasound images, a 3D laser-camera for acquiring digital representations of the external surface of a target region;

input means for receiving an NMR image;

an image processing unit comprising a processor configured to correlate the position of markers on a 3D representation of the target region of a patient and on the diagnostic image of the inside of the target region and to store the result of the correlation in a memory;

The processing unit being configured to carry out image registration of a diagnostic image of the inside of the target region with a representation of the surface of the target region acquired both with markers on the target region and image registration of at least one further representation of the surface of the target region acquired without markers at the later time and to register an ultrasound image with the NMR image based on the registrations carried out matching the NMR image with the representations of the external surface of the target region.

According to sill another embodiment, the system is provided in combination with at least one biopsy tool.

According to still another embodiment the system may be provided with a tracer of the position of the ultrasound probe and/or of the imaged slice in a reference system.

BRIEF DESCRIPTION OF THE DRAWINGS

FIG. 11 is a flow diagram showing the steps of the method according to the present invention.

DETAILED DESCRIPTION OF EMBODIMENTS OF THE INVENTION

Figure 1A:
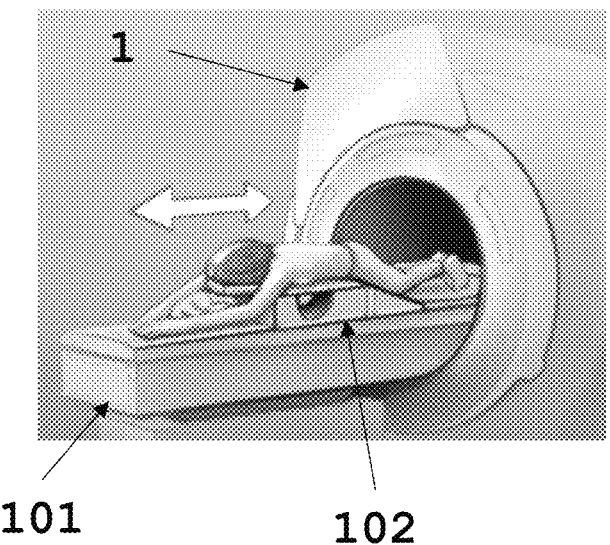
FIGS. 1a and 1b schematically show the typical postures of a patient during breast examination respectively with an MRI apparatus and with an Ultrasound system.
Figure 1B:
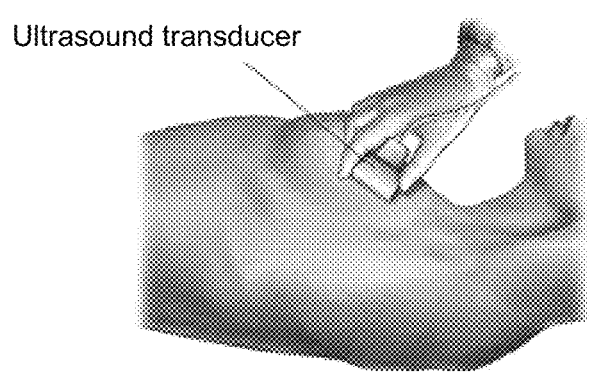

FIGS. 1a and 1b illustrates schematically the posture of a patient during acquisition of diagnostic images of the breast with an MRI apparatus and with an ultrasound imaging system. NMR images provides for high resolution images with a highly detailed reproduction of the tissues. On the other hand the acquisition times, particularly of soft tissues are quite long. In NMR images the different tissues can be better differentiated and recognized. Thus in searching potential lesions in the breast area NMR images are preferred. Ultrasound images have a lower level of detail and tissue diversification but they can be acquired very rapidly allowing real time imaging of a target. This is of advantage when a navigation is required inside the target region for example for tracking moving objects. Thus ultrasound imaging is the preferred technique for tracking and guiding treatment tools, such as for example a biopsy needle or also ablation tools inside the target region towards the specific target tissue. On the other hand while highly echogenic treatment tools may be recognized and differentiated from the tissues of the target region, the different kind of tissues and thus also the target tissue may difficult to be identified in the pure ultrasound image.

Techniques are known to register and combine images obtained from different acquisition apparatus by applying different image acquisition techniques. As a specific example, techniques are known to register and combine NMR images and Ultrasound images of the same target region which are acquired at different times in order to obtain at the same time a good differentiation of the tissue types and thus of the target tissue and real time tracing and guiding of a treatment tool, which is directed to the target tissue in order to carry out a specific task.

When considering particular anatomic target regions, such as for example the breast, the different imaging techniques requires different postures of the patient. Soft tissue target regions will thus suffer of deformations passing from one position of the target region required for a first imaging technique to a second position required for the further imaging technique. In the present example one first imaging technique is MRI and the second imaging technique is ultrasound imaging.

As it appears from FIG. 1A, in a MRI scanner 1, for carrying out breast imaging, the patient lies prone on a table 101. A breast holder 102 is provided having a hollow space for housing downwards hanging breasts.

When acquiring ultrasound images of the breast as it is shown in FIG. 1B, the patient lies supine. The breast is subjected to a different deformation and has a completely different shape as in the prone position during NMR imaging.

The present invention provides for a method and system being able to compensate the changes in shape of the breast when changing posture of the patient.

Figure 1C:
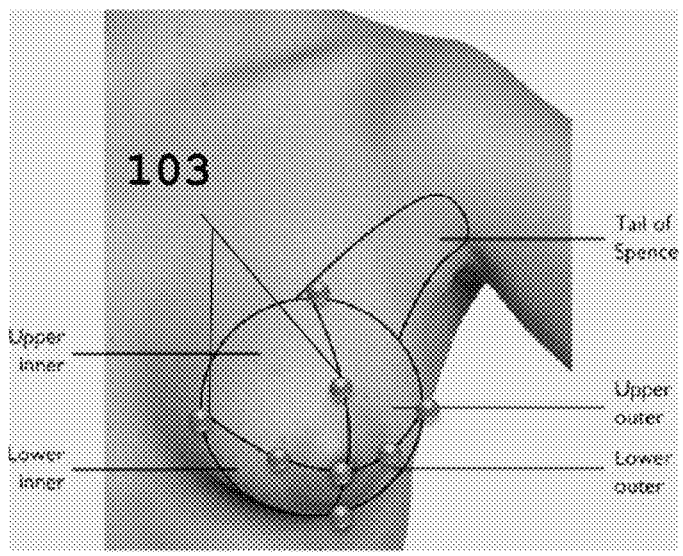
FIG. 1c illustrates typical position for markers on a breast.

At a first time of acquisition of a first NMR image of the breast, a first step of an embodiment of the present invention provides for applying markers on the external surface of the breast. FIG. 1C show markers 103 and a non-limiting example of a pattern of distribution of the markers on the surface of the breast.

According to this non-limiting example, the markers are positioned along the intersection line of a sagittal plane and a coronal plane crossing each other at the nipple. On each side of the nipple two markers are placed. One marker on a coronal plane cutting the base of the breast and one further marker in the intermediate position between the marker on the coronal plane and the marker at the nipple. Different variant of the patter of the described example are possible and may depend also on the specific morphological feature of the breast to be examined.

NMR imaging of the breast is carried out in a conventional manner as known in the art. This acquisition provides a first 3D NMR image as the one represented in FIG. 2 and indicated with NMR. In this image the markers 103 are also shown.

Before or after having acquired the NMR image, during which the patient is in a prone position, the patient is repositioned and a visual image or optical image is acquired of the external surface of the breast on which the markers are present. According to an embodiment the optical or visual image of the external surface of the breast is acquired by using a 3Dlaser camera. This kind of camera is known in the art. In the present method any kind of 3Dlaser camera may be used.

A 3D scanner analyzes a real-world object or environment to collect data on its shape and possibly its appearance (e.g. color). The collected data can then be used to construct digital three-dimensional models. 3D scanners create a point cloud of geometric samples on the surface of the subject. These points can then be used to extrapolate the shape of the subject with a process called reconstruction. Preferred 3D laser scanners are the so called non-contact laser scanners either of the passive or of the active type. Active scanners emit light or other kind if radiation and detect its reflection or radiation passing through object in order to probe an object or environment. Active laser scanners may operate according to different techniques which characterize different types of 3D laser scanners, as for example time of flight laser scanners, triangulation laser scanners, conoscpic holography scanners, structured light scanners, hand held laser scanners, modulated light 3D scanners, and other kind of 3Dlaser scanners. The reconstruction process is a processing step extracting information form the cloud points produces by the scanning process. Also in this case there are known different techniques for reconstructing surface information and generating a 3D virtual image of the shape of the external surface of the target.

Figure 2:
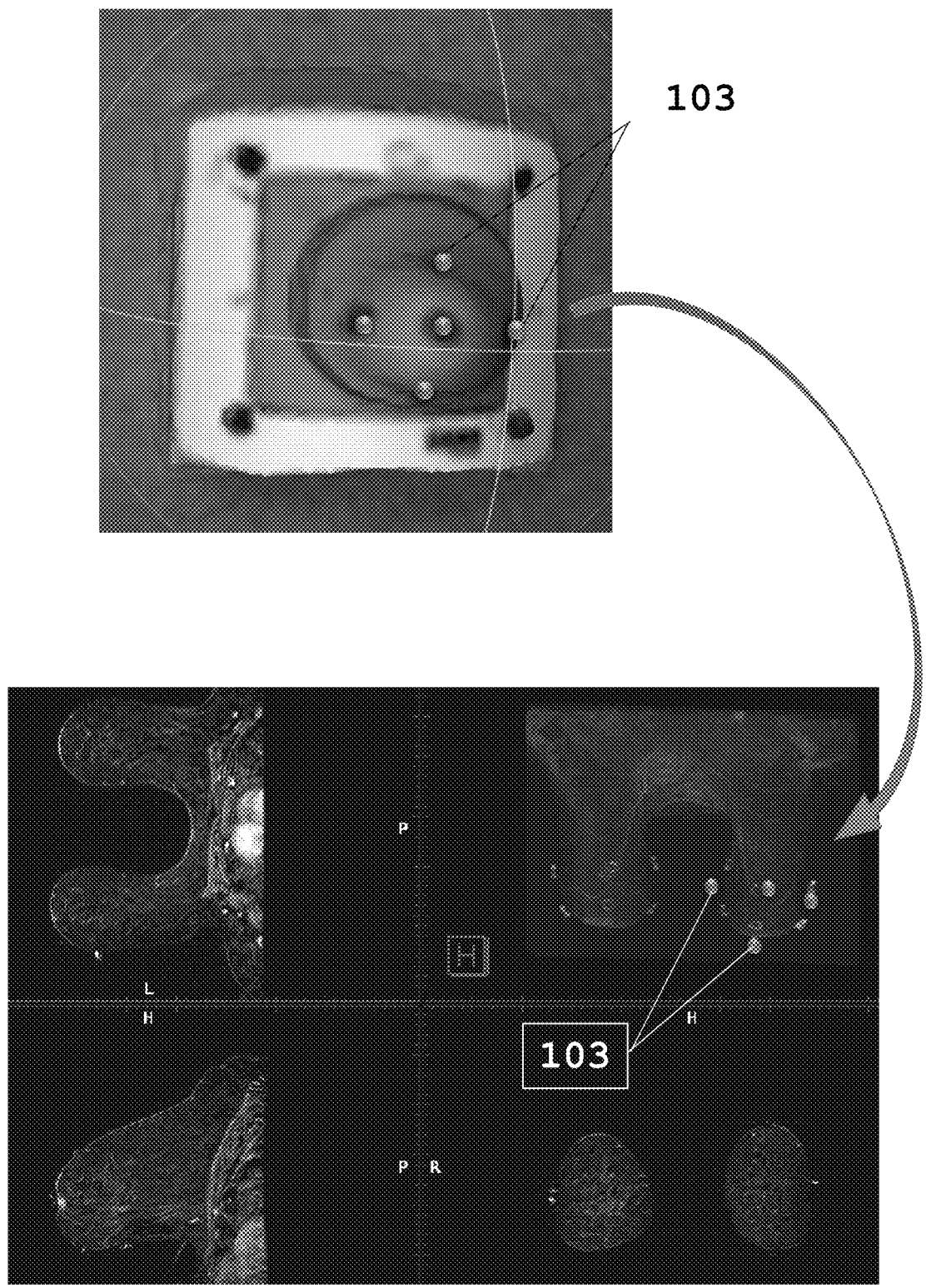
FIG. 2 illustrates the image of a breast with markers obtained by a 3D laser camera and by an MRI apparatus.

FIG. 2 shows in a schematic way by a 2D image the representation of the 3Dimage acquired by the 3D laser scanner with the pattern of markers 103 still on the surface of the breast. This image is indicated by 3DLS. The corresponding MRI image is identified by NMR.

When the 3D volumetric data of the NMR image and the digital representation of the external surface of the breast has been acquired, the positions of the markers 103 are correlated one to the other. This step enables the definition of a transfer function of the map of pixel or voxel of the NMR image in prone position into a computed map of pixel or voxel of the NMR image corresponding to a supine position of the patient.

This involves:

defining each voxel or pixel of the NMR image acquired at time t1 as $$V_{ijk}^{MRI}(x^{MRI}, y^{MRI}, z^{MRI}; t_1).$$

in which:

upper index MRI denotes the image acquired by MRI, j, k are the index of position of the pixel or voxel in an array forming the image and x, y, z are the coordinate of a point in the target region corresponding to the pixel or voxel in relation to a predefined reference system and t1 the time of the acquisition of the NMR image;

defining the pixels or voxels referring to each marker l, with l=1, 2, . . . , n in the NMR image as $$M_l^{MRI}(x_l^{MRI}, y_l^{MRI}, z_l^{MRI}; t_1)$$

and in which:

$$M_l^{MRI} \in V_{ijk}^{MRI},$$

$x_l^{MRI}, y_l^{MRI}, z_l^{MRI}$ are the coordinates of the markers corresponding to the pixel or voxels in the NMR image of the markers at the time of acquisition t1 and in relation to the predefined reference system;

defining the pixels or voxels representing a target in the target region, namely the breast as $$T_{opq}^{MRI}(x_T^{MRI}, y_T^{MRI}, z_T^{MRI}; t_1)$$

in which $$T_{opq}^{MRI} \in V_{ijk}^{MRI},$$

$x_T^{MRI}, y_T^{MRI}, z_T^{MRI}$ are the coordinates of the corresponding pixel or voxel identified by the indexes o,p,q corresponding to the target T in the target region, i.e. the breast, in the NMR image, at the time of acquisition t1 and in relation to the predefined reference system;

further defining as $$V_{ijk}^{O1}(x^{O1}, y^{O1}, z^{O1}; t_1)$$

each voxel or pixel of the optical or visual 3D image of the external surface of the target region, which in the present example is a breast, acquired at the time t1 with a 3D Laser camera, and in which:

upper index O1 refers to the first image acquisition of the externa surface of the target region by a 3D laser camera;

i, j, k are the index of position of the pixel or voxel in an array forming the image of the externa surface of the breast and $x^{O1}, y^{O1}, z^{O1}$ are the coordinate of a point on the external surface of the target region corresponding to the pixel or voxel in relation to a predefined reference system and t1 the time of the acquisition of the NMR image;

defining the pixels or voxels referring to each marker l, with l=1, 2, . . . , n in the 3D scan image of the external surface of the target region as $$M_l^{O1}(x_l^{O1}, y_l^{O1}, z_l^{O1}; t_1)$$

and in which:

$$M_l^{O1} \in V_{ijk}^{O1}$$

$x_l^{O1}, y_l^{O1}, z_l^{O1}$ are the coordinates of the markers corresponding to the pixel or voxels in the image of the external surface of the target region at the time of acquisition t1 and in relation to the predefined reference system.

According to the invention the following steps are carried out:

The map of the position of the markers in relation to a predefined reference system in the NMR image is correlated to the position of markers in relation to a predefined reference system in the image representing the external surface of the breast.

Applying a correlation function Fcor the data allows to construct a transformation function for the pixels or voxels of the NMR image acquired in the prone position to the pixels or voxels in an NMR image of the breast in the supine position.

$$Fcor(M_l^{O1}(x_l^{O1}, y_l^{O1}, z_l^{O1}; t_1), M_l^{MRI}(x_l^{MRI}, y_l^{MRI}, z_l^{MRI}; t_1)) = FTrf;$$

Applying the transformation function Ftrf to the image acquired in the prone position it is possible to compute a model of an NMR image related to the same patient but in the supine position related at the same time of acquisition t1:

$$FTrf(V_{ijk}^{MRI}(x^{MRI}, y^{MRI}, z^{MRI}; t_1), \text{prone}) = V_{ijk}^{MRI,supine}(x^{MRI,supine}, y^{MRI,supine}, z^{MRI,supine}; t_1)$$

The same apply also for the pixels or voxels representing the target in the target region:

$$FTrf(T_{opq}^{MRI}(x_T^{MRI}, y_T^{MRI}, z_T^{MRI}; t_1), \text{prone}) = T_{opq}^{MRI,supine}(x_T^{MRI,supine}, y_T^{MRI,supine}, z_T^{MRI,supine}; t_1)$$

It must be pointed out that in the equations the time t1 of the NMR image acquisition has been used also for the 3D laser scan of the external surface of the breast since this image acquisition is carried out immediately before or after the acquisition of the NMR image.

If in the study of the diagnostic NMR image a potential lesion is individuated, generally a treatment or a biopsy of the lesion is requested. This intervention is normally carried out at a later time t2 different in relation to the time t1 at which the NMR image was acquired. Furthermore the treatment tool or the biopsy needle are guided by an ultrasound system which allows to carry out real time imaging of the target region, i.e the breast and to image the tool displacements inside the target region for guidance of the tool onto the target tissue to be treated. Ultrasound imaging requires a supine posture of the patient.

According to an embodiment of the invention illustrated schematically in FIG. 3, at this later time, identified by t2, before carrying out treatment under guidance of ultrasound imaging, a new digital representation of the external surface of the breast indicated as O2 is carried out by a 3D laser camera, thereby obtaining an image comprising pixels or voxels defined as $$V_{ijk}^{O2}(x^{O2}, y^{O2}, z^{O2}; t_2)$$

wherein:

upper index O2 refers to the second image acquisition of the external surface of the target region by a 3D laser camera, j, k are the index of position of the pixel or voxel in an array forming the image of the externa surface of the breast, and $x^{O2}, y^{O2}, z^{O2}$ are the coordinate of a point on the external surface of the target region corresponding to the pixel or voxel in relation to a predefined reference system, and T2 the time of the acquisition of the image of the external surface of the target region.

At this time t2 no marker is applied to the target region, i.e. to the breast.

As a further step of a method according to the present invention, a surface matching between the optical or visual images of the external surface of the target region, i.e. of the breast acquired at times t1 and t2 is carried out. This surface matching uses the digital representations of the external surface of the breast defined above and furnishes the matched data according to the following equation:

$$Fsm(V_{ijk}^{O2}(x^{O2}, y^{O2}, z^{O2}; t_2), V_{ijk}^{O1}(x^{O1}, y^{O1}, z^{O1}; t_1)) = V_{ijk}^{SM}(x^{SM}, y^{SM}, z^{SM}; t_1) \Rightarrow Ftrf, \text{supine}_{t1 \to t2}$$

in which:

$V_{ijk}^{SM}$ are the pixels or voxels of the image representing the external surface of the breast acquired in the second scan O2 and matched with the image representing the external surface of the breast acquired in the first scan O1;

$x^{SM}, y^{SM}, z^{SM}$ are the coordinate of the points represented by the pixels or voxels in relation to a predefined reference system From the above data a transfer function prone-supine is computed Ftrf,supine$_{t1 \to t2}$ which function matches the NMR image transformed for the supine posture of the patient at time t1 in an NMR image transformed for the supine posture of the patient at time t2. Applying this transformation leads to $$Ftrf,supine_{t1 \to t2}(V_{ijk}^{MRI,supine}(x^{MRI,supine}, y^{MRI,supine}, z^{MRI,supine}; t_1)) = V_{ijk}^{MRI,supine}(x^{MRI,supine}, y^{MRI,supine}, z^{MRI,supine}; t_2)$$

in which the upper index MRI,supine refers to the transformation of the NMR image from the original prone position of the patient to the supine position of the patient at time t1 and t2 denotes the fact that a further transformation constructed on the surface matching of the two images of the external surface of the breast O1 and O2 has been carried out.

When considering the pixels related to the target and their position the position of the target in an image based on the NMR image acquired at t1 in prone position and transformed for the supine position at time t1 and further matched with a later image O2 acquired in the supine position of the patient is calculated as $$Ftrf,supine_{t1 \to t2}(T_{opq}^{MRI,supine}(x_{opq}^{MRI,supine}, y_{opq}^{MRI,supine}, z_{opq}^{MRI,supine}; t_1)) = T_{opq}^{MRI,supine}(x_{opq}^{MRI,supine}, y_{opq}^{MRI,supine}, z_{opq}^{MRI,supine}; t_2)$$

in which opq are the indexes identifying the pixel of the target T and $x_T^{MRI,supine}, y_T^{MRI,supine}, z_T^{MRI,supine}$, the upper index MRI,supine refers to the transformation of the NMR image from the original prone position of the patient to the supine position of the patient at time t1 and t2 denotes the fact that a further transformation constructed on the surface matching of the two images of the external surface of the breast O1 and O2 has been carried out. At this stage of the method according to the present invention, the transformed NMR image $V_{ijk}^{MRI+US,supine}$ can be registered with ultrasound images acquired in the supine position of the patient and at time t2. Having subjected the originally acquired NMR image related to the prone position of the patient into an image containing NMR image data, which is represented by pixels or voxels of the first acquired NMR image having been only topologically displaced relatively to one another and to a reference system for being matched with the deformation occurred to the breast in changing position from prone to supine and this match having been further updated to the new supine position in the later imaging session allows to carry out the registration process of the ultrasound images with the NMR image in a more precise manner compensating the possible errors generated by the change in shape of the breast in the different posture of the patient.

According to a further step of the method of the present invention, after the above steps ultrasound images of the target region are acquired. Defining the pixels or voxels of the ultrasound image or of a time sequence of ultrasound images which can be 3D images or 2D images as $$V_{ijk}^{US}(x^{US}, y^{US}, z^{US}; t_2)$$

in which:

the upper index US refers to the kind of imaging technique, namely ultrasound imaging, i, j, k are the index of position of the pixel or voxel in an array forming the image of the breast and $x^{US}, y^{US}, z^{US}$ are the coordinate of a point on the external surface of the target region corresponding to the pixel or voxel in relation to a predefined reference system and t2 the time of the acquisition of the ultrasound image or of the sequence of ultrasound images The registration and combination of this ultrasound image or these ultrasound images is carried out by means of a registration and image combination or image fusion function:

$$FRegcomb(V_{ijk}^{MRI,supine}(x_{ijk}^{MRI,supine}, y_{ijk}^{MRI,supine}, z_{ijk}^{MRI,supine}; t_2), V_{ijk}^{US}(x^{US}, y^{US}, z^{US}; t_2)) = V_{ijk}^{MRI+US,supine}(x^{MRI+US,supine}, y^{MRI+US,supine}, z^{MRI+US,supine}; t_2)$$

The obtained image data are related to the combination of the NMR imaged data transformed for the supine position and matched with the supine position at the second time t2, with the ultrasound image data, in which:

FRegcomb is the registration and combination function, $V_{ijk}^{MRI,supine}$ the upper index MRI,supine refers to the transformation of the NMR from the original prone position of the patient to the supine position of the patient respectively at time t1 and t2, $x^{MRI,supine}, y^{MRI,supine}, z^{MRI,supine}$ are the coordinate of the position of the image pixels or voxels, $V_{ijk}^{MRI+US,supine}$ are the registered and combined pixels or voxels of the NMR image $V_{ijk}^{MRI,supine}$ with the ultrasound image/images $V_{ijk}^{US}$.

$x^{MRI+US,supine}, y^{MRI+US,supine}, z^{MRI+US,supine}$ the coordinate of the pixels or voxels of the registered and combined images.

This applies similarly also for the pixels or voxels and their coordinate representing the target T in the target region $$FRegcomb(T_{opq}^{MRI,supine}(x_T^{MRI,supine}, y_T^{MRI,supine}, z_T^{MRI,supine}; t_2), V_{ijk}^{US}(x^{US}, y^{US}, z^{US}; t_2)) = T_{opq}^{MRI+US,supine}(x_T^{MRI+US,supine}, y_T^{MRI+US,supine}, z_T^{MRI+US,supine}; t_2)$$

in which:

FRegcomb is the registration and combination function, $T_{opq}^{MRI,supine}$ the upper index MRI,supine refers to the transformation of the NMR image from the original prone position of the patient to the supine position of the patient respectively at time t1 and t2, $x_T^{MRI,supine}, y_T^{MRI,supine}, z_T^{MRI,supine}$ are the coordinate of the position of the image pixels or voxels representing the target, $T_{opq}^{MRI+US,supine}$ are the registered and combined pixels or voxels of the NMR image of the target $T_{opq}^{MRI,supine}$ with the ultrasound image/images $V_{ijk}^{US}$;

$x_T^{MRI+US,supine}, y_T^{MRI+US,supine}, z_T^{MRI+US,supine}$ the coordinate of the pixels or voxels of the registered and combined images of the target.

Figure 4:
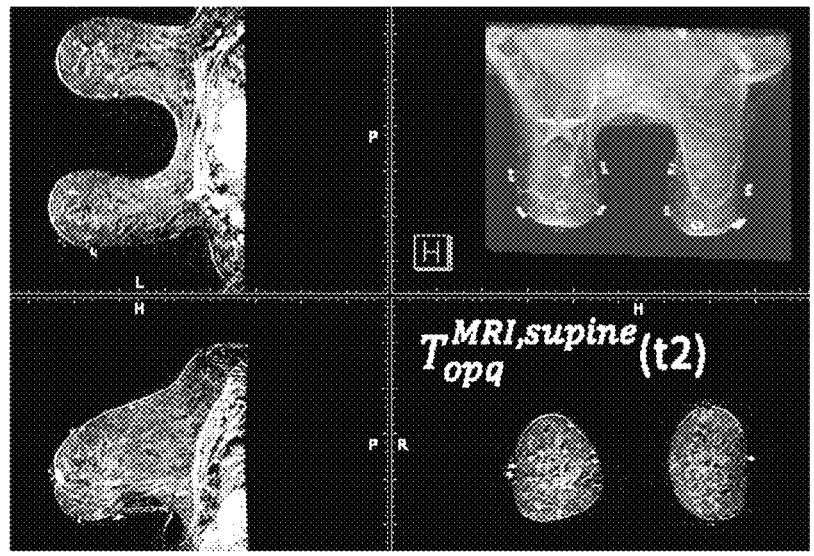
FIG. 4 illustrates the 3D image obtained by an MRI and the two-dimensional slice image containing the lesion extracted from the 3D image.
Figure 4:
Figure 4:
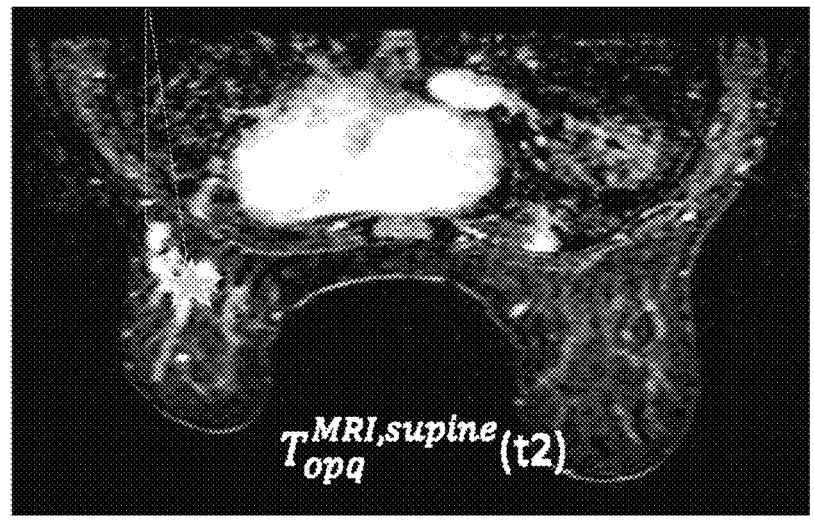

FIG. 4 shows the two dimensional image along a slice of the 3D NMR image at the end of the transformations according to the above embodiment of the method.

For computing the correlation transition and matching function disclosed above several different methods and algorithm are available which can be used alternatively or in combination, registration and correlation of the marker position may be computed by means of several techniques and/or surface matching and/or registration of the digital image acquired by the two different imaging techniques is carried out by means of one of the following methods or by combination of the methods such as intensity based registration methods comparing intensity patterns in images via correlation metrics, feature-based methods find correspondence between image features such as points, lines, and contours, registration methods using rigid or elastic transformations such as transformations using radial basis functions, transformations using physical continuum models as fluid dynamic models of viscous fluids or method based on diffeomorphisms models, methods using similarity measures such as cross-correlation, mutual information sum of squared intensity differences and ratio image uniformity, methods based on measure matching, curve matching, surface matching vi mathematical currents and varifolds. The list gives only some examples of the models and method used to carry out the image processing steps of the method according to the present invention and the possible methods and techniques for carrying out the correlation between the marker positions, computing the transition equations and matching surfaces and also registering images shall not be considered limited with the above listed ones.

It has also to be noted that advantageously the guiding of the treatment tool necessitates only to have clearly highlighted in the ultrasound images the position of the target tissue of a suspected lesion or similar so that in order to correctly guide the tool at this target tissues no detailed visual image is required but the sole position in the image of the voxels or pixels representing the target tissue. This allows to limit the information to be subjected to transition and transformations since only identification of certain pixels or voxels or of their position in the ultrasound images is needed. Highlighting of these pixels or voxels may be carried out in several ways as for example giving a certain colour or generating a line encircling or delimiting a ROI or a region of the image containing the image voxels representing the target tissue.

Figure 5:
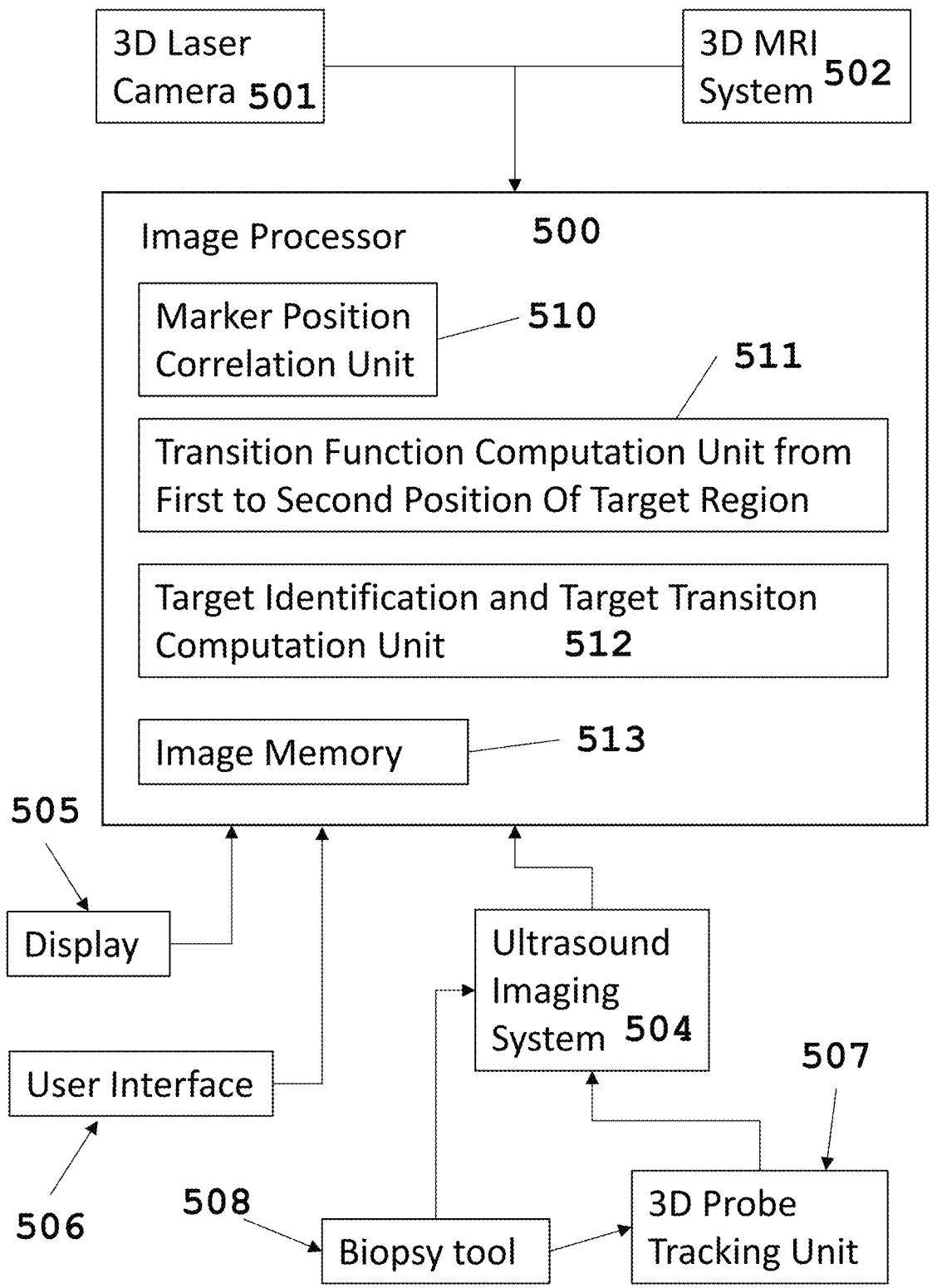
FIG. 5 is a block diagram of an embodiment of the system according to the present invention.

FIG. 5 show an embodiment of a system according to the present invention. An image processor 500 is provided which is configured to carry out the method steps disclosed above. The image processor has connection ports to a 3D laser camera 501 and to a 3D MRI system 502. Furthermore, the image processor 500 has a port for connecting to an ultrasound imaging system 504. To one or more displays 505 and to user interfaces 506 which can be one or more of the known interfaces with processing units such as a mouse, a keyboard, voice interface, gesture interface, touchscreens and a combination thereof. The list not being exhaustive but cites only some examples out of the plenty of different interface devices. The ultrasound system 504 is connected to an ultrasound probe 507. Many different kind of ultrasound probes may be used in combination with the present invention. In the illustrated embodiment, a 3D probe in combination with a probe tracking unit is shown.

According to an embodiment, the ultrasound system may be connected directly or may associated to a treatment tool 508 like for example an ablation tool or a biopsy needle. According to an embodiment the tool can be provided with tags and in combination with a tool tracing system which can be an independent one or the same tracking system of the 3D ultrasound probe.

According to an embodiment, the image processor 500 comprises a processing unit configured to carry out an image processing software. The image processing software when executed by the processing unit configures the processing unit and the peripherals in operating units carrying out the steps of the method according to the present invention as the method of the embodiment described above in relation to FIGS. 3 and 4.

According to the embodiment of FIG. 5, the execution of the image processing software configures the image processor and the peripherals by having:

a Marker Position correlation Unit 510 which calculates the correlation function between the marker position in the NMR image and the marker position in the 3D surface image as defined above with $$Fcor(M_I^{O1}(x_I^{O1},y_I^{O1},z_I^{O1};t_1),M_I^{MRI}(x_I^{MRI},y_I^{MRI},z_I^{MRI};t_1))$$

a transition Function Computation Unit which computes out of the correlation function Fcor a transition function which transforms the image data of the target Region from the first to the second Position, namely prone and supine according to the transformation function $$FTrf(V_{ijk}^{MRI}(x^{MRI},y^{MRI},z^{MRI};t_1),\text{prone}) = V_{ijk}^{MRI,supine}(x^{MRI,supine},y^{MRI,supine},z^{MRI,supine};t_1)$$

a target identification and target transition Computation Unit 512 which applies the transition function to the pixels representing the target in the NMR image and in the 3D scan image. According to an embodiment, the unit 512 operates according to the method steps of the embodiment described in relation to FIGS. 3 and 4, an image memory 513 for saving the images acquired at each acquisition and processing step for example according to the embodiment of the method described with reference to FIGS. 3 and 4, an image combination or fusion unit combining the NMR image data acquired at a different earlier time and subjected to transition between prone and supine position of the patient with the Ultrasound image data acquired in real time in a second time for tracing and/or guiding at least a treatment tool which has to be brought with its operating tip in at a target positioned in the target region.

The embodiment of the system according to FIG. 5 links functionally different units need not to be present at the same time, since the method is related to combine together image data acquired with two different imaging modes at different time and allowing to compensate the deformation of the target region determined by the different postures of the patient required by the two imaging modes. Thus the NMR system 502 and the 3D laser camera 501 must not be a part of the system but may be different and separate apparatus having a direct or indirect interface with the image processor 500. With direct interface, it is meant a physical communication interface using cables and receiving and transmitting communication units or using wireless connection by means of wireless receiving and transmitting communication units. With the term, indirect interface, it is meant any data support in which the image data acquired by the MRI system and the 3D laser camera is saved in order to be used at a second time, for being processed according to the method of the present invention. Such data support may be in the form of a portable memory, a memory in a centralized patient managing system like a Pacs or similar, a CD, DVD or any other kind of rewritable or non rewritable memory supports.

Similarly in relation to the image processor 550, this processor may be a separate apparatus like a computer, a workstation or a centralized server, as a PACS or similar or the image processor is integrated in one of the apparatus 501, 502, 504, preferably in the Ultrasound imaging system 504. In this case one variant embodiment provides for a dedicated hardware for the image processor 500, while another variant embodiment provides for an image processor 500 whose hardware is at least partially the same hardware which controls the ultrasound imaging system for generating the ultrasound images.

Also in relation of the tracking system 507 of the ultrasound probe and of the biopsy tool 508 or other kind of treatment tools, various embodiments may be provided according to different variants embodiments. In one variant embodiment, the tracking unit 507 may be integrated in the ultrasound imaging system 504 either as separate additional hardware or as partially using the hardware provided in the ultrasound imaging system 504 and dedicated to the generation of the ultrasound images.

Figure 3:
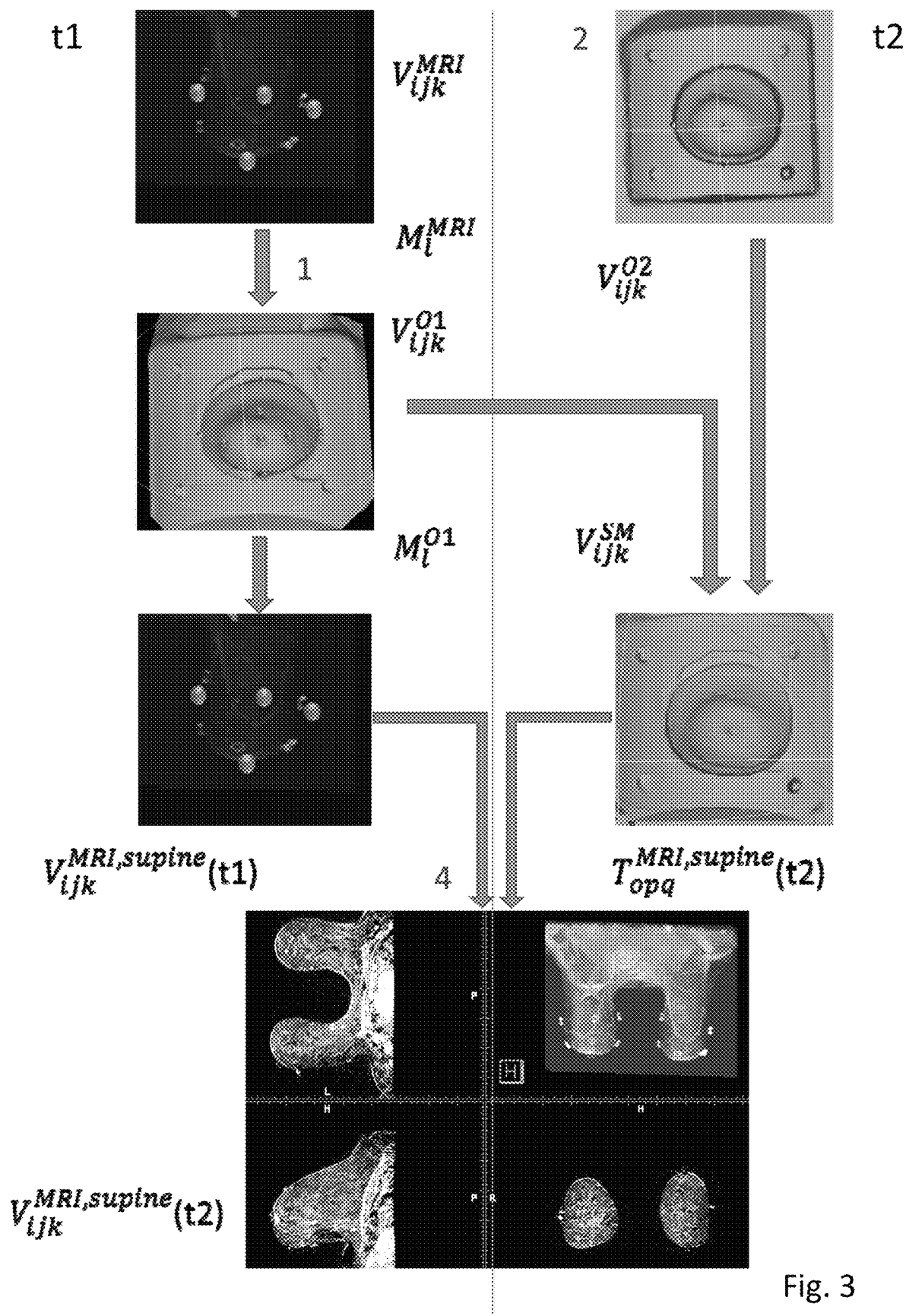
FIG. 3 illustrates schematically by means of the images acquired in each step, the process according to the present invention.

FIG. 11 provides for a description of the steps described according to FIGS. 3 and 4 and carried out in view of an example by the system according to FIG. 5 which description is directed to the example of the searching and treating lesion in a breast. At step 1100 and at time t1 patient starts the examination. Markers are applied to the surface of the breast at step 1101, for example according to the embodiment of FIG. 1c. At 1102 the patient is positioned in a supine position as shown in FIG. 1B. The three dimensional (3D) image of the external surface of the breast is acquired with the patient in supine position by means of a 3D laser camera at step 1103. Patient is positioned in an MRI system in a prone position as shown in FIG. 1a at step 1104 and the NMR image is acquired in the following step 1105. The next step 1106 consists in analysing the high definition NMR-image in order to individuate potential lesions. This may be carried out alternatively or in combination by direct visual examination of the image by the doctor or by any kind of known Computer Diagnostic Aid systems. Examples of these systems uses several predictive algorithms such as neural networks or similar as disclosed for example in US2007233624, US2006098876 or WO2009007285. If the result is negative, because no lesion is found the decision at step 1107 determined the end of the examination 1108.

If a suspect lesion is discovered in the image at step 1107 the patient is disinvited to attend a second examination phase which is carried out at a later time t2 as indicated by 1110. In this second examination phase generally a biopsy of the target, i.e. of the suspect lesion is carried out in order to determine by means of biochemical analysis if the tissue considered a suspect lesion is really such. A tissue sample has to be taken by an invasive intervention consisting in guiding a so called biopsy needle with its operative tip at the target tissue considered a suspect lesion. The insertion and the guiding of the biopsy needle is best carried out by using an ultrasound imaging system and acquiring ultrasound real time images of the target region where the supposed lesion is located. Since ultrasound imaging is a real time imaging technique but does not have good details of the suspect lesions, while this details are represented in the NMR image a combination of the images has to be carried out in order to clearly show the lesion position inside the ultrasound images, so that the biopsy needle is correctly guided against the target tissue. Furthermore the ultrasound imaging of the breast id generally carried out with the patient in supine position. This determines a deformation of the breast and a displacement of the position of the target tissue when passing from the prone to the supine position of the patient.

Thus according to the present embodiment of the invention starting the second phase 1110 of the examination at a later time t2 than the one t1 when the first phase has been carried a further 3D surface image of the breast is taken at 1111 with the patient in a supine position.

At step 1112 a surface matching is carried out between the 3D laser scans executed in the first phase at time t1 and indicated as scan (A) and the one in the second phase at time t2 indicated as scan (B). Surface matching allows to consider variation of posture between the two supine postures at time t1 and t2 and to compute a transformation of the image pixels or voxels from the image acquired at t1 and the images acquired al t2.

At step 1113 the NMR image acquired in prone position with markers is transformed in an NMR image corresponding to a patient in a supine position, i.e. in the supine position of the 3D scan (A) acquired at time t1 in the first examination phase. The surface matching with scan (B) transforms further the NMR image in an NMR image related to a supine position of the patient which supine position corresponds to the one at the second phase at time t2. This allows to locate exactly the position of the target tissue, i.e. the suspect lesion in an ultrasound image by combining the ultrasound images with the NMR images transformed for a supine position of the patient and matched with the supine position at the second examination phase as indicated by 1114. Since the biopsy needle is echogenic when carrying out the ultrasound imaging the image of the target tissue and of the biopsy needle are best shown in the combined NMR and ultrasound images.

According to an embodiment, the combination of the NMR image and of the Ultrasound images may be limited to the pixels or voxels related to the target tissue or no combination at all is carried out but only the pixels or voxels which corresponds to the target tissue are determined by means of the NMR image which pixels or voxels are identified in the ultrasound image and highlighted as target tissue in the ultrasound image.

Several embodiments regarding the systems and methods for guiding biopsy needle or other treatment tools to a target region are known. According to one embodiment of the present invention described with reference to FIG. 6, a method for guiding a surgical tool by ultrasonic imaging, comprises the steps of:

(a) acquiring in real-time a sequential plurality of 3D ultrasonic images of a target area;

(b) defining in real-time an orientation and position of the tool and a direction of a characteristic working axis of the tool;

(c) defining in real-time the position of a working end of the tool along said direction of said characteristic axis;

(d) determining the relative position in space of each of the 3D ultrasonic images of the time sequence of images and the direction of the characteristic axis of the tool for each of said 3D images;

(e) defining, for at least one of the 3D ultrasonic images acquired in the time sequence, a 2D image plane which intersects the corresponding 3D ultrasonic image and is perpendicular to the direction of the characteristic axis of the tool determined in real-time and is spaced a predetermined distance forward of the working end of the tool with reference to the orientation and position of the tool upon acquisition of the corresponding 3D ultrasonic image;

(f) generating a real-time 2D image using the corresponding 3D ultrasonic image of the sequence of 3D ultrasonic images along said 2D image plane, wherein the position of the characteristic axis of the tool is indicated in said 2D image, and wherein the 2D image includes indications of the position of the target tissue to be treated by said tool. The last step being carried out by applying the steps of combining the NMR image data transformed relatively to the supine position of the patient ad to the supine posture at the second time of the second examination phase with the 3D ultrasound images or with the 2D images of the slices identified according to the above steps.

According to an embodiment, the method is carried out with a device for guiding surgical tools by real-time ultrasonic imaging, comprising:

(a) an ultrasound system for acquiring in real-time a sequential plurality of 3D ultrasonic images of a target area;

(b) a system for determining in real-time and tracking of the position and orientation of a surgical tool and for defining in real-time the direction of a characteristic axis of the tool corresponding to the detected position and orientation of the tool;

(c) a unit for determining in real-time the position of a working end of the tool along said direction of said characteristic axis;

(d) a system for determining the relative position in space of each 3D ultrasonic image and the direction of the characteristic axis of the tool corresponding to each 3D ultrasonic image; and (e) a unit for generating, for one or more of the 3D ultrasonic images acquired sequentially, a real-time 2D image defined by a 2D image plane that intersects a corresponding 3D ultrasonic image, which 2D image plane is perpendicular to the direction of the characteristic axis of the tool determined in real-time and is spaced a predetermined distance forward of the working end of the tool with reference to the orientation and position of the tool upon acquisition of the corresponding 3D ultrasonic image, said 2D image being generated using the corresponding 3D ultrasonic image;

(f) a monitor and a unit for displaying said real-time 2D image on said monitor, said real time 2D image being from the point of view of the tool, wherein the 2D image is from a point of view at or near said characteristic axis of the tool, wherein the intersection of the characteristic axis of the tool and the 2D image plane is indicated in said 2D image, and wherein the position of the target to be treated by said tool is also indicated in said 2D image.

A system for guiding surgical tools by real-time ultrasonic imaging is very schematically shown in FIG. 1.

Numeral 608 designates an ultrasonic scan probe which is connected to a probe control unit for ultrasonic imaging and particularly for generating volumetric ultrasound images. A variety of volumetric ultrasound imaging methods are known. According to a known method, the probe is provided in combination with a tracking system which detects the position, orientation and displacement of the probe. A succession of ultrasound images is acquired as the probe is moved, said images being grouped into a 3D image composed of the various 2D images acquired at different probe positions along the displacement path, which positions are detected by the tracking system. Thus, the 2D images can be arranged in relative order to form a 3D image.

Tracking systems are known and widely used for the purpose of acquiring a 3D ultrasound image. An example of tracking system is the system sold by Ascension Technology with the trade name PCI Bird which is incorporated in a currently available product, sold by the owner hereof with the name of "Virtual Navigator".

Figure 6:
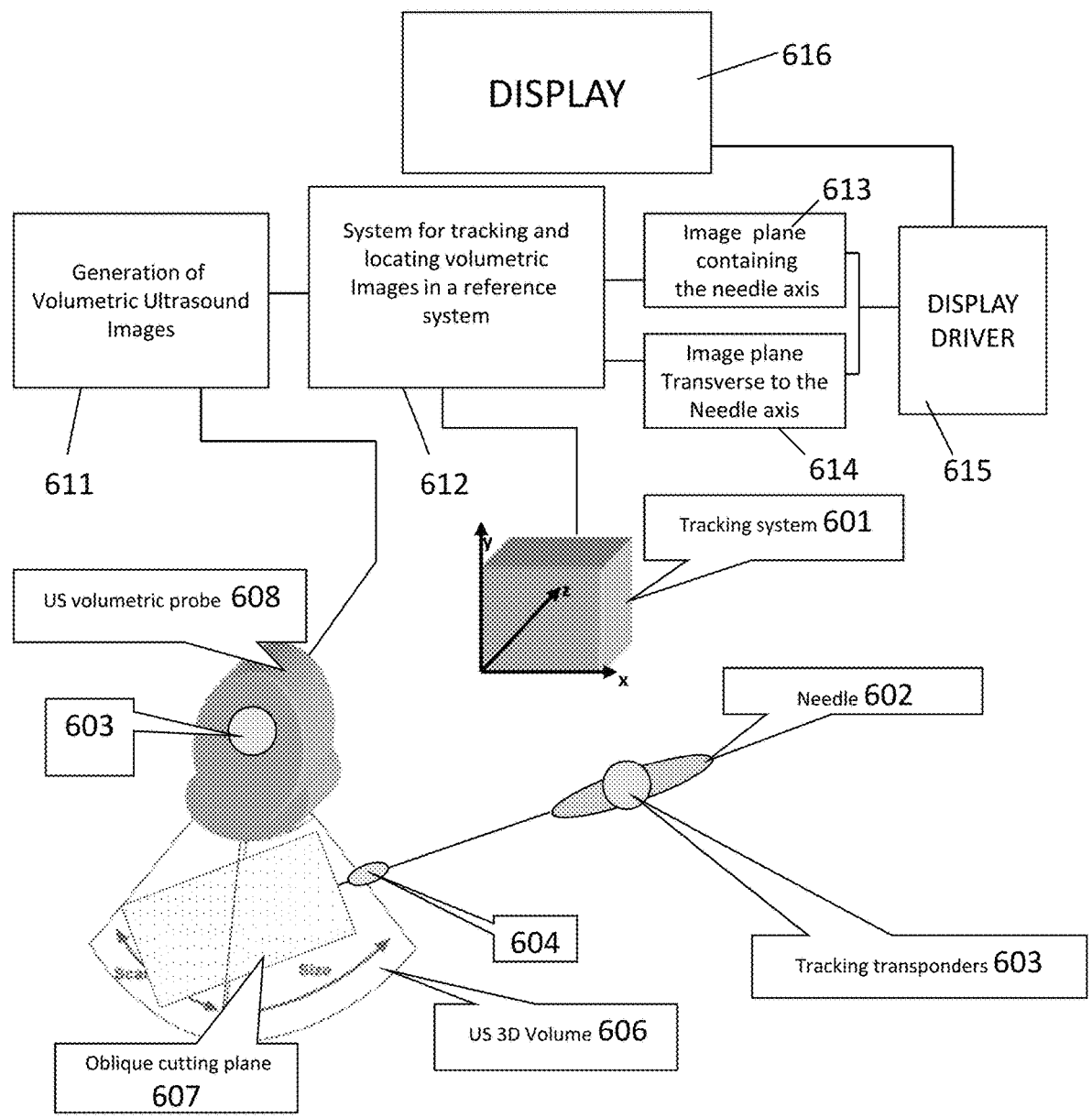
FIG. 6 is a schematic representation of an embodiment of an ultrasound system for tracking a biopsy needle.

In the scheme of FIG. 6, the tracking system is represented by the coordinate system designated by numeral 601. The tracking system actually defines the various positions of the probe 608 with reference to a predetermined initial reference point and is thus the operating unit that defines a reference system describing the probe displacement space.

In principle, there is no limitation as for the type of probe to be used, provided that it can cover a slice area large enough to contain the image to be acquired. Nonetheless, as shown in FIG. 6, advantages are achieved from using a volumetric probe. A volumetric probe may be as disclosed in EP 1 681 019 and in EP 1 167 996 by the owner hereof.

Thus, when the size of the subject to be imaged by ultrasound allows to do so, the probe is not required to be manually displaced by the operating personnel or a specially dedicated device. In other cases, the volumetric probe can be displaced less often and to few different positions, in which it can be held during automatic acquisition of the volumetric image that the probe can generate without being displaced.

In this case, the tracking system 601 is only used to define the different probe position/s in the space described by the reference system generated or defined by the tracking system 601 itself.

The tracking systems require at least one detector to be mounted to the element whose displacement or position is to be monitored, which marker/detector, with reference to the tracking system used herein, is a transponder. A transmitter-receiver unit can detect the marking transponder and determine the probe position. The marker means associated with the probe 608 are designated by numeral 603.

Numeral 606 designates the volumetric image acquired by the volumetric probe 608.

Numeral 602 designates a surgical tool and particularly a needle or similar elongate, rod-like element. These tools may include, for example, biopsy needles, cannulas for insertion of a variety of devices, thermoablation needles or the like.

The needle or rod-like element has a characteristic functional axis, and in this case this axis is the axis of the needle which coincides with the insertion axis. Different types of tools may have different characteristic functional axes. For example, in the case of a surgical knife, the characteristic working axis may be the cutting edge of its blade. The characteristic functional axis of a particular type of tool can be determined in an intuitive and simple manner. The needle 602 may carry a single sensor or marking transponder, which is sufficient to determine the position of the tool and its orientation, particularly with reference to the characteristic working or functional axis of said needle which, as mentioned above, is the central longitudinal axis of the needle. However, according to the improvement of the figures, the tool, i.e. the needle 602 carries two or more sensors or marking transponders, designated by numerals 603, 604. This improvement allows detection of any needle bending, which can be thus accounted for while operating the system. Therefore, in the case of the needle 602 of the figures, two transponders are located at a certain distance from each other, coincident with the needle axis, and can be used to determine the needle orientation with particular reference to the insertion direction, as well as any deformation, particularly bending or curving of the needle. When a transponder is mounted directly to the tip or at a predetermined distance therefrom, the position of the needle tip can be determined upon insertion into the body under examination. The sensor or transponder at the tip of the needle 602, here the transponder 604, shall not necessarily be placed at the tip but, as mentioned above, it may be located at a predetermined known distance from the tip. In this case, once the position of the transponder 604 has been detected, the position of the tip may be determined by a simple arithmetic operation.

Numeral 607 designates a cutting plane of the 3D image that has a predetermined inclination relative to the characteristic functional axis, i.e. the longitudinal central axis, i.e. the direction of insertion of the needle 2. A 2D image of the object is generated along said cutting plane, using the image data of the 3D image. This process consists in determining the subset of voxels of the 3D image that falls within the predetermined cutting plane 607, to generate a 2D image. This may occur in a known manner, as disclosed for instance in the above mentioned patent applications by the applicant hereof, and particularly in EP 1 167 996.

Processing occurs in a control and processing unit typically incorporated in ultrasonic imaging apparatus, which substantially consists of a processing unit that stores and executes special ultrasound apparatus control programs for transmitting and receiving ultrasound signals, for focusing the ultrasound signals transmitted by the probe and the ultrasound signals received by the probe upon reflection of the transmitted signals, for converting the received signals into image data and for generating and displaying images on a monitor, as well as for monitoring the execution of other operations that depend on the ultrasound signal acquisition and processing mode being used. The processing unit also controls the tracking system, which may be provided as software or dedicated hardware controlled by said software.

In FIG. 6, the processing unit is designated by its functional blocks only, which are generally used to execute the operations of the present invention. Thus, the block 611 generally includes all hardware and software units required for 3D imaging (see also EP 1 681 019 and EP 1 167 996). Thanks to the tracking system, the 3D image is assigned a well-defined position in a reference Cartesian system, which is defined by the tracking system that detects the position of the probe 608. The tracking system simultaneously detects the position of the needle or other tool 602 and the orientation of the characteristic functional axis of such tool 602 with reference to the same reference system defined by the tracking system. This will provide well-defined relative positions between the volumetric image and the position and orientation of the tool 602, i.e. the characteristic functional axis thereof. In these conditions, a cutting plane may be defined in the 3D or volumetric image generated by the probe 608, which plane has a predetermined inclination relative to the characteristic functional axis of the tool 602.

Multiple cutting planes may be also defined, having predetermined and different positions and orientations relative to said characteristic functional axis of the tool 602.

Particularly, referring to the needle, a cutting plane may be defined, which is oriented perpendicular to the characteristic functional axis of the tool 602 and is at a predetermined distance from the internal or front end tip, with reference to the direction of insertion of the needle. In this case, the image generated along said cutting plane and reconstructed from the volumetric image data, i.e. the voxels that fall within such cutting plane will be as viewed by an observer situated at the tip of the needle and looking towards the longitudinal axis of the needle in the direction of insertion of the latter.

Alternatively to or in combination with the above, images may be also generated along different cutting planes.

A possible additional cutting plane might be the plane that contains the longitudinal axis of the needle 602, with the path of the needle into the body under examination being thus visible.

The images obtained along the various cutting planes may be displayed in succession, i.e. alternate to each other or in side-by-side or simultaneous arrangement. This condition is shown by the functional blocks 613 and 614, which designate all hardware and software units required to define the above mentioned cutting planes and generate images along said cutting plane, as well as simultaneously or alternately display them using display drivers 615 on the display 616.

The use of a volumetric probe 608 allows the above process to be accomplished in a very short time, wherefore imaging may be deemed to occur in real time.

Figure 7:
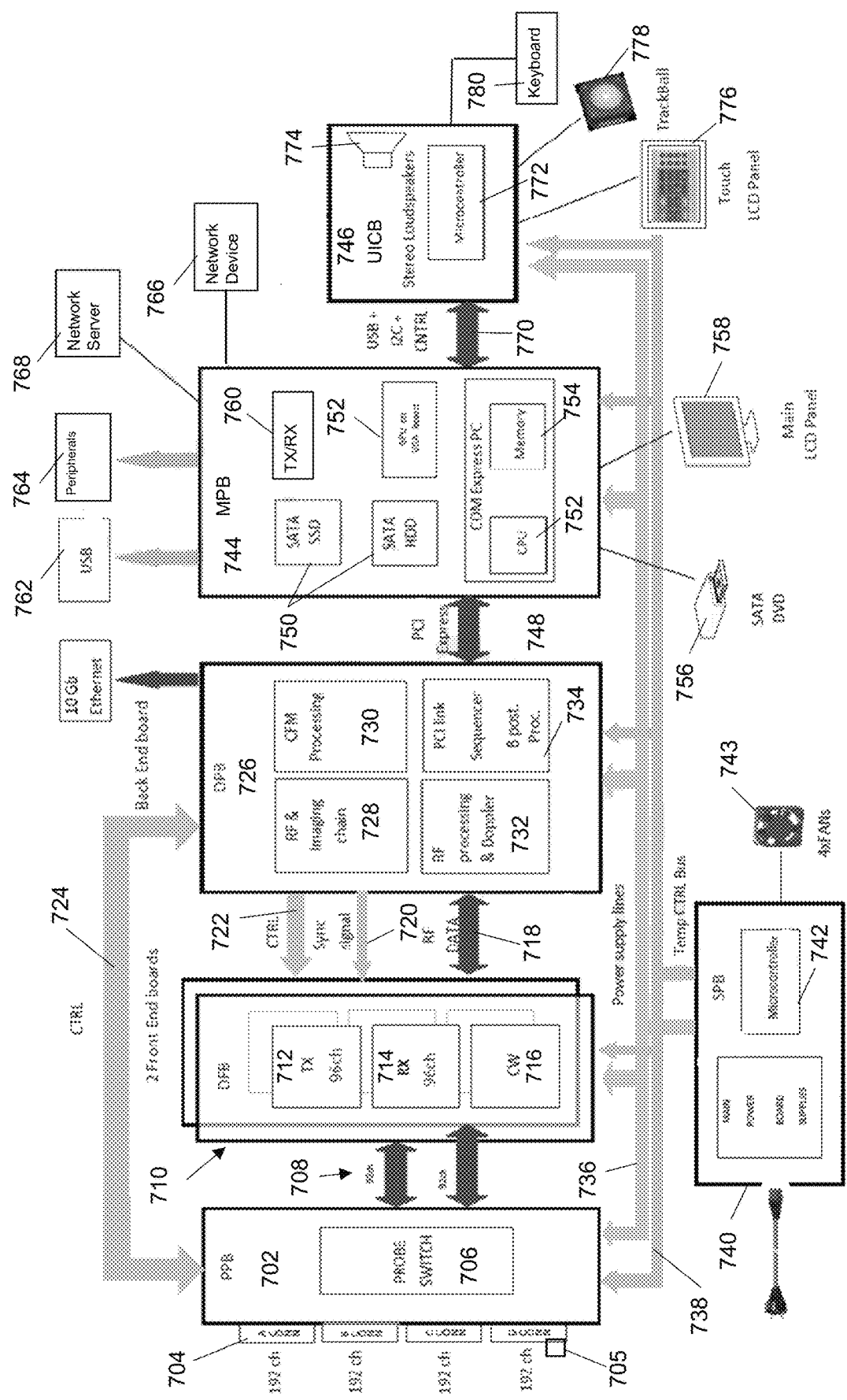
FIG. 7 illustrates a block diagram of an ultrasound system formed in accordance with an embodiment of the invention.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a select one of the connection ports 704. The connect signal may be generated by the probe when power is initially supplied to the probe when coupled to the connection port 704. Additionally or alternatively, each connection port 704 may include a sensor 705 that detects when a mating connection on a cable of a probe has been interconnected with the corresponding connection port 704. The sensor 705 provides be ca connect signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front end boards 710 include receive beamformer circuits 714 that received echo/receive signals and perform various analogue and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front end boards 710 may convert the RF ultrasound data to I,Q data pairs which are then passed to the digital processing board 726.

The digital processing board 726 includes an RF and imaging module 728, a color flow processing module 730, an RF processing and Doppler module 732 and a PCI link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like. The network server 768 may represent also a separate image processor according to the embodiment of FIG. 5 of the present invention.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
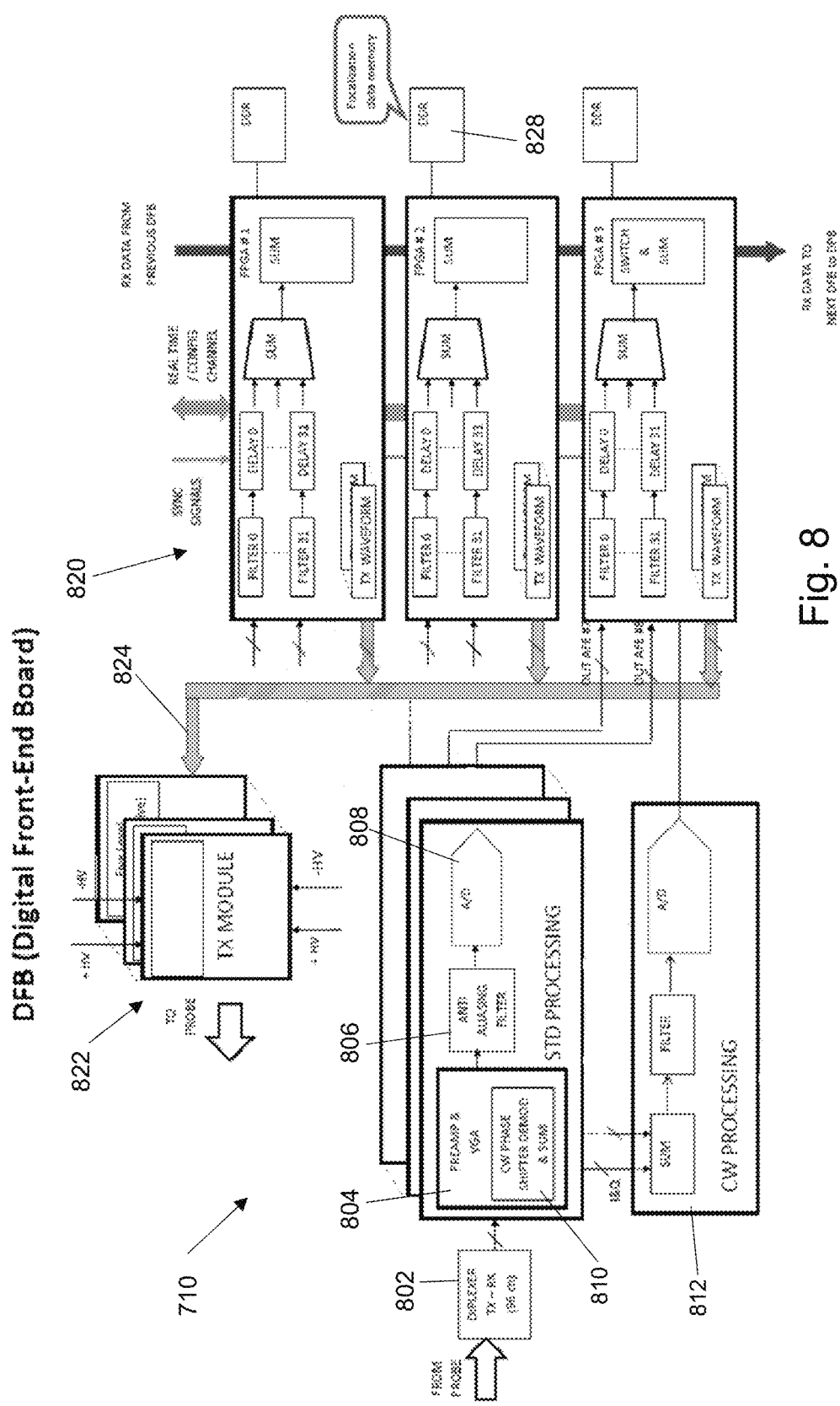
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering. The output thereof is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The being formed RF data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
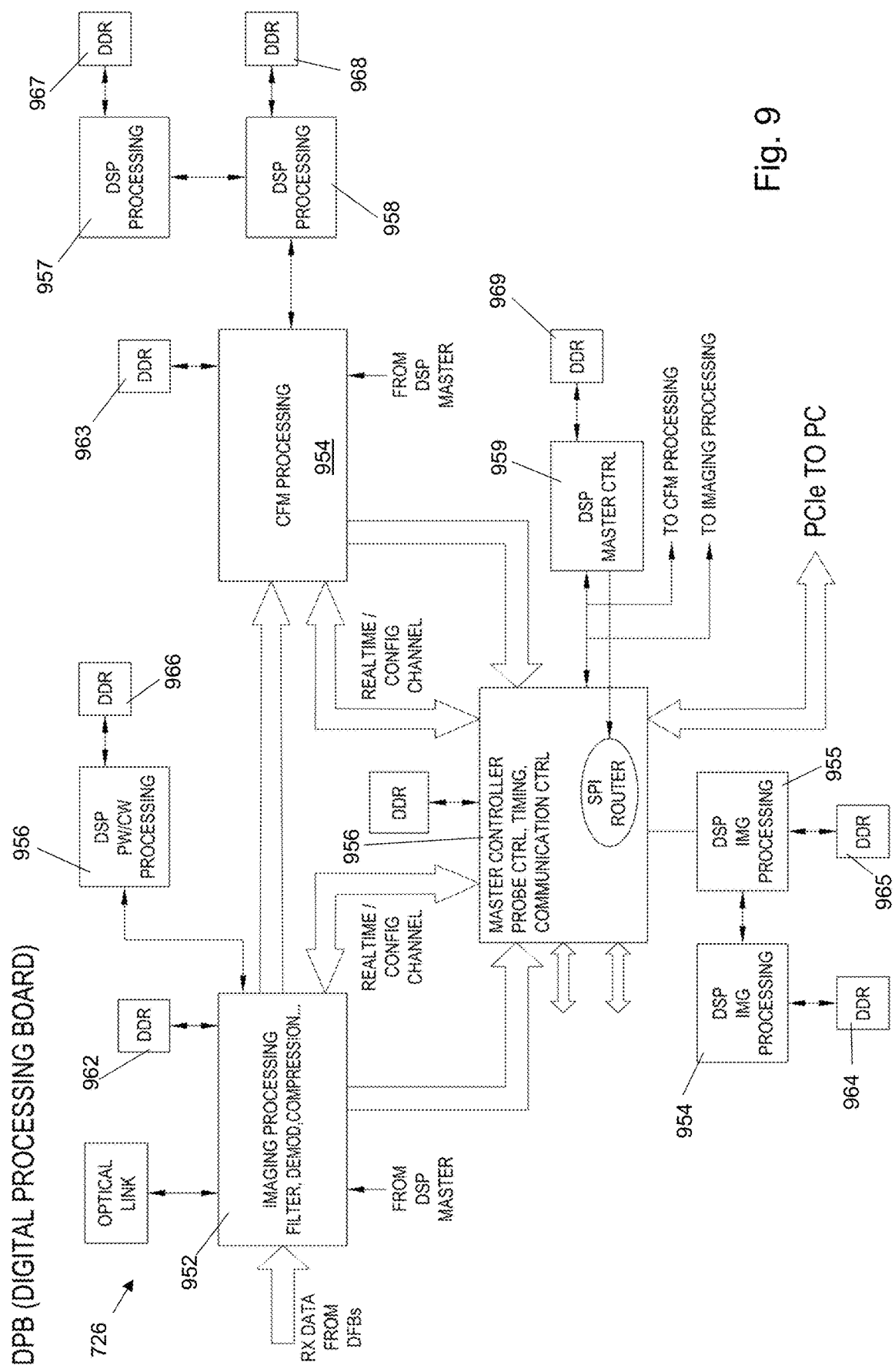
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 950 provides real-time configuration information and synchronization signals in connection with each channel to the digital front-end board 710.

The digital processing board might be also configured to carry out image processing according to the ones described with reference to the embodiments of FIGS. 3, 4 and 11 and take over at least in part the functions of the image processor 500 described with reference of FIG. 5. A image processing software being loaded or loadable on the digital processing board and being executed by said digital processing board which configures the board and the peripherals controlled by the board to operate according the image processor described with reference to FIG. 5.

Figure 10:
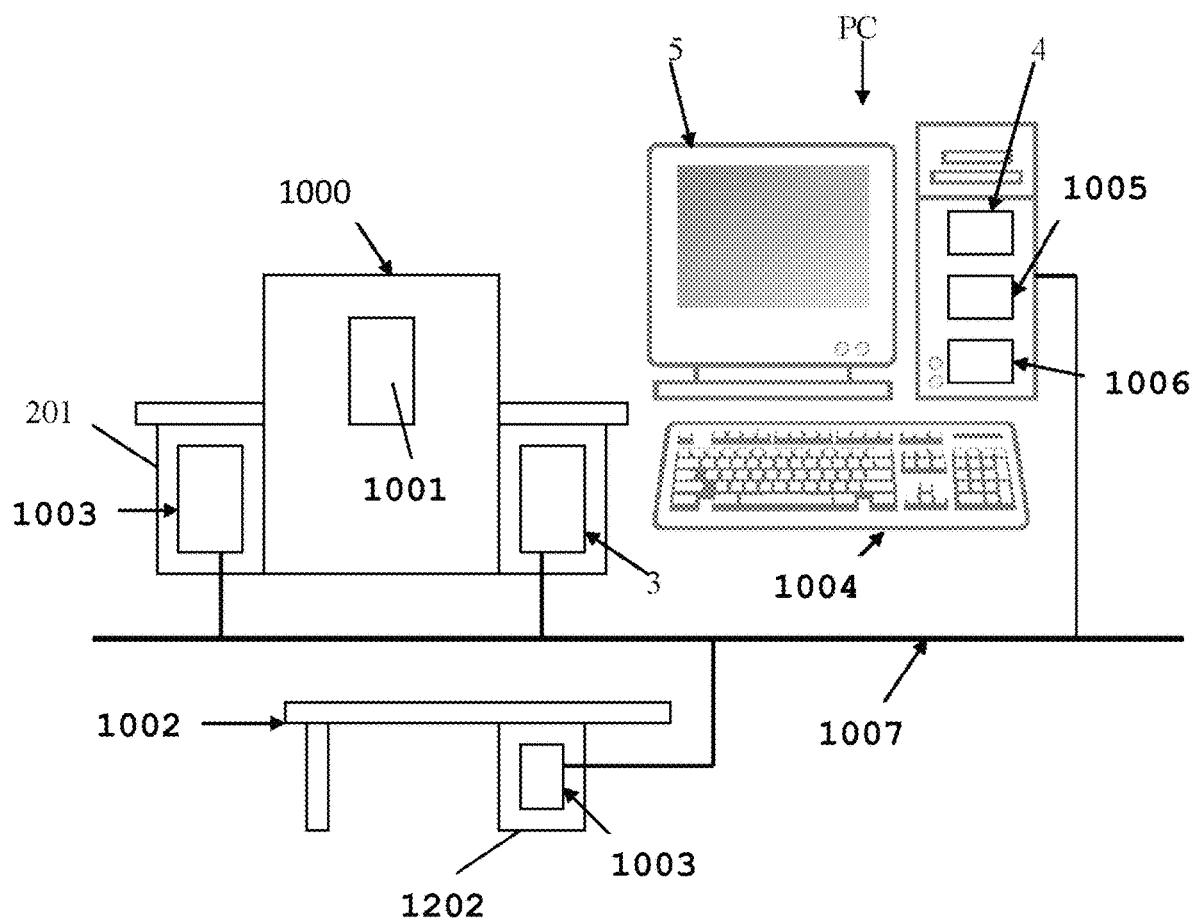
FIG. 10 is a schematic block diagram of an embodiment of an MRI system.

FIG. 10 is a schematic view of an embodiment of a Nuclear Magnetic Resonance imaging apparatus according to the invention. With reference to FIG. 1, a Nuclear Magnetic Resonance imaging machine comprises a signal exciting and receiving unit consisting of a magnetic unit 1000. The magnetic unit includes permanent or resistive or superconducting magnets for generating a static field inside a cavity 1001 which is designed to receive the patient body or a part thereof, particularly a limited anatomic region, such as a leg, an arm, the head, etc.

As it is generally known, different coils are associated to the static field generating magnet, including:

excitation coils, for exciting nuclear spins;

magnetic gradient generating coils, for selecting the section plane along which imaging has to be performed, for encoding nuclear spins to univocally identify the signals transmitted at a predetermined space position and univocally assign the received data to a predetermined pixel of a pixel matrix which forms the displayed image;

receiving coils, for receiving magnetic resonance echoes. Also, other means are provided, such as temperature control sensors and/or means for heat increase or generation and means for heat dissipation, which are designed to set and maintain a predetermined operating temperature, etc.

All the above elements are well-known and widely used in Nuclear Magnetic Resonance imaging machines of any type and size, both for total body machines, i.e. those designed to accommodate the whole patient body or a substantial part thereof, and for dedicated machines, i.e. those adapted to only accommodate specific limbs or limited parts or regions of the patient body. The geometry of the magnetic structure, i.e. of the cavity for accommodating the body under examination or the part thereof may also be of any type, and particularly either of the open C- or U-shaped type, or consisting of two poles separated by columns, or of the annular, closed type.

The shown machine has a closed, i.e. annular magnetic structure and the cavity is only open at the two end sides transverse to the axis. A patient table or seat, which may have any construction and is denoted with numeral 1002, is generally associated to the magnetic unit. Particularly, the patient table or seat 1002 may have a structure adapted to form closable housing compartments, as is schematically shown in FIG. 10.

The magnetic unit or structure, with the above mentioned components, is associated to control, monitoring and processing units, which have the function to control and adjust the various components of the magnetic structure and to receive and process echo signals to extract therefrom all data useful for the reconstruction thereof into an image formed by an array of light image dots, the so-called pixels or voxels, the brightness and/or color of which are univocally related to the received data and whose position is related to the position, within the body part under examination, wherefrom the echo signal was transmitted. Particularly, and as a rule, an electronic unit 1003 for controlling the signal exciting and receiving devices, a unit 1004 for entering commands to the signal exciting and receiving unit, a display and image processing unit 1005 and a filing and storage unit 1006 are associated to the magnetic unit.

The unit 1006 for controlling the signal exciting and receiving devices is at least partly contained in the case of the magnetic unit 1000 and/or possibly also at least partly contained within the structure of the patient table 1002, in one part thereof 1202, for instance a support column, having the form of a switchboard. The units for entering commands 1004 to the signal exciting and receiving units, for display and image processing 1005 and for filing and storage 1006 are included, partly as hardware peripherals and partly as software programs, in a traditional personal computer. The communication between the unit 1003, contained in the case of the magnetic unit and/or in the structure of the patient table, with the units 1004, 1005, 1006 of the control console provided by the personal computer is obtained by means of a communication bus denoted with numeral 1007. The communication bus may be of any type, e.g. a conventional communication bus of the Ethernet type, of the SCSI or USB type or of any other type, which allows multiplex communication among several units. Once the type of bus to be used is selected, the implementation of interfaces with the bus 1007 on the individual units 1003, 1004, 1005, 1006 is well-known in the art.

As it appears from the preceding description, the MRI system may comprise hardware units which can be used at least in part to carry out specific tasks of the image processor 500 described with reference to the embodiment of FIG. 5 and also of the boards controlling the ultrasound imaging system. By loading and carrying out a software program the same boards used by the MRI system may also be configured to operate and carry out the image processing steps according to the present invention and alternatively or in combination one or more tasks related to the tracking system, and/or to the Ultrasound system, combining the three four systems MRI, Ultrasound image processing and probe and/or tool tracing system in one device having centralized processing hardware and software.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method of postural independent location of targets in diagnostic images acquired by multimodal acquisitions, comprising:
    generating a transition of a digital image of an inside of a target region from a first to a second position of the target region by correlating a position of markers placed on an external surface of the target region in the digital image of the inside of the target region and in a first digital representation of an external surface of the target region acquired by optical scanning the external surface; and
    at a later time, registering a first diagnostic image of the inside of the target region, which has been transitioned into the second position, with a second diagnostic image of the target region acquired with the target region in the second position by matching a second representation of the external surface of the target region in the second position without markers with the first diagnostic image of the inside of the target region, which has been transitioned into the second position, further comprising:
    placing the markers on the external surface of the target region undergoing diagnostic imaging, wherein the markers are responsive to optical radiation and to at least an additional imaging technique for imaging the inside of the target region;
    acquiring, by the optical scanning of the target region, the first digital representation of the external surface of the target region together with the markers, with the target region in the first position;
    acquiring the first diagnostic image of the inside of the tar e t region or of a region of interest (ROI) inside the target region together with the markers by the additional imaging technique with the target region in the second position in space;
    performing a correlation between the first diagnostic image of the inside of the target region or of the ROI and an optical representation of the external surface of the target region by correlating the positions of the markers in the first diagnostic image of the inside of the target region or of the ROI and on the optical representation of the external surface of the target region;
    at a later time, acquiring by the optical scanning of the target region, a second digital representation of the external surface of the target region without the markers and with the target region in the first position;
    carrying out a surface matching between the first and the second digital representations of the external surface of the target region;
    computing a transition of the digital image of the inside of the target region from the second position in space to the first position in space by applying the correlation and obtaining a digital image of the inside of the target region transitioned to the first position;
    matching the digital image of the inside of the target region transitioned to the first position with the second digital representation of the external surface of the target region to locate a target; and
    performing ultrasound imaging of the target region with the target region in the first position in space to obtain an ultrasound image and registering the ultrasound image with the digital image of the inside of the target region transitioned to the first position and matched with the second digital representation of the external surface in the first position.

2. The method according to claim 1, wherein at least one of the first or the second diagnostic images is produced with a diagnostic imaging technique selected from the group consisting of MRI, CT, CBCT, PET, and Ultrasound.

3. The method according to claim 1, wherein the first diagnostic image of the inside of the target region is a 3D-image of a predetermined volume.

4. The method according to claim 1, wherein at least one of the first or the second digital representations of the external surface of the target region is acquired by a 3D laser scan of the external surface.

* * * * *